United States Patent
Blume et al.

(10) Patent No.: US 9,926,451 B2
(45) Date of Patent: Mar. 27, 2018

(54) SILANE-MODIFIED SILICIC ACID, METHOD FOR THE PRODUCTION AND USE THEREOF

(71) Applicants: Anke Blume, Weilerswist (DE); Torsten Peterle, Grenzach-Wyhlen (DE); Jaroslaw Monkiewicz, Rheinfelden (DE)

(72) Inventors: Anke Blume, Weilerswist (DE); Torsten Peterle, Grenzach-Wyhlen (DE); Jaroslaw Monkiewicz, Rheinfelden (DE)

(73) Assignee: Evonik Degussa GmbH, Essen (DE)

( * ) Notice: Subject to any disclaimer, the term of this patent is extended or adjusted under 35 U.S.C. 154(b) by 0 days.

(21) Appl. No.: 15/102,487

(22) PCT Filed: Dec. 16, 2014

(86) PCT No.: PCT/EP2014/077859
§ 371 (c)(1),
(2) Date: Jun. 7, 2016

(87) PCT Pub. No.: WO2015/091412
PCT Pub. Date: Jun. 25, 2015

(65) Prior Publication Data
US 2016/0326374 A1 Nov. 10, 2016

(30) Foreign Application Priority Data
Dec. 17, 2013 (DE) .................. 10 2013 226 162

(51) Int. Cl.
| C09C 1/30 | (2006.01) |
| B60C 1/00 | (2006.01) |
| C01B 33/193 | (2006.01) |
| C07F 7/18 | (2006.01) |
| C08K 9/06 | (2006.01) |
| C01B 33/18 | (2006.01) |

(52) U.S. Cl.
CPC .......... C09C 1/3081 (2013.01); B60C 1/0016 (2013.01); C01B 33/193 (2013.01); C07F 7/1836 (2013.01); C08K 9/06 (2013.01); C01B 33/18 (2013.01); *C01P 2004/51* (2013.01); *C01P 2004/61* (2013.01); *C01P 2006/12* (2013.01)

(58) Field of Classification Search
CPC .................................................. C09C 1/3081
See application file for complete search history.

(56) References Cited

U.S. PATENT DOCUMENTS

| 6,268,424 B1 | 7/2001 | Blume et al. |
| 2006/0254463 A1 | 11/2006 | Luginsland et al. |
| 2007/0059232 A1* | 3/2007 | Stenzel ................. B60C 1/0016 423/335 |

FOREIGN PATENT DOCUMENTS

| DE | 103 58 466 A1 | 8/2004 |
| EP | 1 590 297 A2 | 11/2005 |

OTHER PUBLICATIONS

International Search Report dated Mar. 4, 2015, in PCT/EP2014/077859 Filed Dec. 16, 2014.
Wong, et al., "Filler-Filler Interaction and Filler-Polymer Interaction in Carbon Black and Silica Filled Exxpro™ Polymer," Macromolecular Symposia, vol. 194, No. 1, 2003 XP055171628 (10 Pages).
Wolff, "Chemical Aspects of Rubber Reinforcement by Fillers," Rubber Chemistry and Technology, vol. 69, 1996, XP009058797 (22 pages).
Goerl, et al., "Silanisierte Kieselsaeuren—Eine neue Produktklasse fuer zeitgemaesse Mischungsentwicklung," Kautschuk + Gummi Kunststoffe, vol. 46, No. 7, 1993, XP 000384142 (7 pages).
Wolff, "Optimization of Silane-Silica OTR Compounds. Part 1: Variations of Mixing Temperature and Time During the Modification of Silica with Bis-(3-Triethoxisilylpropyl)-Tetrasulfide," Rubber Chemistry and Technology, vol. 55, No. 4, 1982, XP008175116 (23 pages).
Sae-Oui, et al., "Roles of silane coupling agents on properties of silica-filled polychloroprene," European Polymer Journal, vol. 42, No. 3, 2006, XP028029977 (8 pages).

* cited by examiner

*Primary Examiner* — Kuo Liang Peng
(74) *Attorney, Agent, or Firm* — Oblon, McClelland, Maier & Neustadt, L.L.P.

(57) ABSTRACT

The invention relates to silane-modified silicas having a BET surface area of 40 to 155 m²/g, a sulphur content between 0.05% and 25% by weight and a particle size d5 of ≥4 μm, and d50 of ≥16 μm.
The silane-modified silicas are used in rubber mixtures.

17 Claims, No Drawings

SILANE-MODIFIED SILICIC ACID, METHOD FOR THE PRODUCTION AND USE THEREOF

The invention relates to a silane-modified silica, to a processes for preparation thereof and to the use thereof.

It is known that oxidic or silicatic compounds can be treated with organosilicon compounds in order through this treatment to strengthen the bond between inorganic filler and the organic polymer used in filler-reinforced elastomers and hence to improve the properties of the fillers in the polymers.

DE 2141159, DE 2212239 and U.S. Pat. No. 3,978,103 disclose that sulphur-containing organosilicon compounds, such as bis(3-triethoxysilylpropyl)tetrasulphane or 3-mercaptopropyl-triethoxysilane, are used as a silane adhesion promoter or reinforcing additive in oxide-filled rubber mixtures, for applications including tyre treads and other parts of automobile tyres.

It is known that coupling agents for tyre parts that can be used in order to avoid the considerable problems in the processing, for example pre-scorch, scorch and plasticity characteristics, of mercaptosilanes are usually polysulphidic organosilanes, for example bis(3-triethoxy-silylpropyl)tetrasulphane or bis(3-triethoxysilylpropyl)-disulphane (DE 2542534, DE2405758, DE19541404, DE19734295), which constitute a compromise in relation to vulcanization resistance, ease of preparation and reinforcement performance for silica-filled vulcanizates.

The known introduction of the corresponding additives, specifically of the organosilanes and the unmodified fillers into the unvulcanized polymer mixtures can be effected in different ways.

The in situ method involves a combined mixing operation of fillers, such as carbon black and silica, with organosilanes and the polymers used.

The ex situ method involves modification of the filler with the corresponding organosilane or a mixture of various organosilanes before the filler is processed with the polymer to give the crude rubber mixture.

It is also known that organosilanes can be metered in liquid form (U.S. Pat. No. 3,997,356) in the course of crude mixture production for rubber mixtures, or else that the active filler can be metered in via a preformed physical mixture of organosilane and filler (DE 3314742, U.S. Pat. No. 4,076,550). A disadvantage of these blends which have not been thermally pretreated is the lack of storage stability and hence the frequent lack of stability in the properties of the products.

U.S. Pat. No. 4,151,154 describes oxidic silicatic fillers, the surface of which has been subjected to a treatment with two different types of organosilicon compounds. This involves treating the oxidic particles such that they exhibit a relatively high affinity for water and can also be distributed more easily in aqueous systems.

U.S. Pat. No. 3,567,680 discloses modification of kaolin suspended in water with various organosilanes. However, the organosilicon compounds described are water-soluble in the amounts needed for the modification, and so the treatment of the filler in this case can be effected from an aqueous solution.

U.S. Pat. No. 4,044,037 describes aryl polysulphides and mineral fillers which have been treated with these compounds and are used in rubber mixtures. The preparation is effected in an aqueous/alcoholic formulation containing 80 to 99.9% by weight of alcohol.

Moreover, EP-C 01 26 871 discloses a process in which the surface of silicatic fillers is modified with the aid of an aqueous emulsion of water-insoluble organosilicon compounds.

It is known that the surface of fillers can be modified through dissolution of the organosilicon compound in an organic solvent and subsequent treatment of these fillers, for example clays (U.S. Pat. No. 3,227,675).

EP 1590297 and EP 1585704 disclose precipitated silicas having low surface area.

DE 10122269.6 discloses a process for reacting at least one biopolymeric, biooligomeric, oxidic or silicatic filler with at least one silane in a compressed gas.

The known fillers modified ex situ with organosilanes have the disadvantage that the dispersions of these fillers modified ex situ are very poor, which leads to elevated Mooney viscosities and poor abrasion resistance.

It is an object of the present invention to provide a silane-modified silica which has excellent dispersancy and as a result has improved rubber properties, for example abrasion, vulcanization characteristics and Mooney viscosity.

The invention provides a silane-modified silica, which is characterized in that the BET surface area is 40 to 155 $m^2/g$, preferably 50 to 135 $m^2/g$, more preferably 80 to 130 $m^2/g$, the sulphur content is between 0.05% and 25.00% by weight, preferably between 0.05% and 10.00% by weight, more preferably between 0.05% and 4.00% by weight, and the particle size d5 is ≥4.05 µm, preferably ≥4.10 µm and <8 µm, more preferably ≥4.12 µm and <6 µm, and d50 is ≥16.0 µm, preferably ≥17.5 µm and <26.0 µm, more preferably ≥19.0 µm and <28.0 µm.

The silane-modified silica may have a $d_{median}$ of >20.0 µm, preferably >20.3 µm, more preferably >20.6 µm.

The inventive silane-modified silica may have a content of carbon in pure or chemically bound form between 0.1% and 25% by weight, preferably between 0.1% and 10% by weight, more preferably between 0.1% and 5% by weight.

The inventive silane-modified silica may have a content of physically and chemically bound alcohol between 0% and 25% by weight, preferably between 0% and 15% by weight, more preferably between 0.1% and 10% by weight.

The inventive silane-modified silica may have a residual content of alcohol originating from the silane, in chemically or physically bound form, of less than 75 mol %, preferably less than 50 mol %, more preferably less than mol %, especially preferably less than 20 mol %, of the starting amount of the alcohol in the silane used.

The inventive silane-modified silica may contain 0.1% to 50% by weight, preferably 0.1% to 25.0% by weight, more preferably 0.1% to 10% by weight, of silane.

The inventive silane-modified silica may contain 50% to 99.9% by weight of silica, preferably precipitated silica.

The silane may be bound chemically and/or physically, preferably chemically, to the surface of the silica.

The inventive silane-modified silica may contain SCN groups.

The invention further provides a process for preparing a silane-modified silica, which is characterized in that at least one silica having a BET surface area of 40 to 175 $m^2/g$, preferably 50 to 155 $m^2/g$, more preferably 80 to 150 $m^2/g$, and a particle size d5 of ≥4 µm, preferably ≥4.05 µm and <8 µm, most preferably ≥4.07 µm and <6 µm, and d50 of ≥16 µm, preferably ≥17.5 µm and <24.0 µm, more preferably ≥19 µm and <22.0 µm, is reacted with at least one sulphur-containing silane.

The silica may have a $d_{median}$ of >18.0 µm, preferably >19.0 µm, more preferably >21.0 µm.

The silica may have Sears numbers (consumption of 0.1 N KOH) between 1 and 50 ml per 5 g of sample.

The sulphur-containing silane used may be an organosilicon compound or mixtures of organosilicon compounds of the general formula (I)

$$Z\text{-}A\text{-}S_x\text{-}A\text{-}Z \qquad (I)$$

in which x is a number from 1 to 14, preferably 1 to 8, more preferably 2 to 5,

Z is $SiX^1X^2X^3$ and $X^1$, $X^2$, $X^3$ may each independently be hydrogen (—H), halogen (—Cl, —Br, —I) or hydroxyl (—OH), an alkyl substituent, preferably methyl-, ethyl-, propyl- or butyl-, an alkyl acid substituent $(C_xH_{2x+1})$—C(=O)O—, alkenyl acid substituent, for example acetoxy-$CH_3$—(C=O)O—, a substituted alkyl acid substituent or alkenyl acid substituent, for example oximato-$R^1{}_2C$=NO—, a linear or branched, cyclic hydrocarbon chain having 1-8 carbon atoms, a cycloalkyl radical having 5-12 carbon atoms, a benzyl radical or a halogen- or alkyl-substituted phenyl radical, alkoxy groups, preferably ($C_1$-$C_{24}$) alkoxy, more preferably methoxy-($CH_3O$—) or ethoxy-($C_2H_5O$—), and also dodecyloxy-($C_{12}H_{25}O$—), tetradecyloxy-($C_{14}H_{29}O$—), hexadecyloxy-$C_{16}H_{33}O$—) and octadecyloxy-($C_{18}H_{37}O$—), having linear or branched hydrocarbon chains having ($C_{1-24}$) atoms, alkoxy groups having linear or branched polyether chains having $C_1$-$C_{24}$ atoms, a cycloalkoxy group having ($C_{5-12}$) atoms, a halogen- or alkyl-substituted phenoxy group or a benzyloxy group, A is a linear or branched, saturated or unsaturated, aliphatic, aromatic or mixed aliphatic/aromatic divalent $C_1$-$C_{30}$-comprising hydrocarbon chain, preferably $C_1$-$C_3$, more preferably (—$CH_2$—), (—$CH_2$—)$_2$, (—$CH_2$—)$_3$, (—$CH(CH_3)$—$CH_2$—) or (—$CH_2$—$CH(CH_3)$—).

A may be linear or branched and may contain saturated and unsaturated bonds. Rather than having hydrogen substituents, A may have a wide variety of different substituents, for example —CN, halogens, for example —Cl, —Br or —F, alcohol functionalities —OH, alkoxides —$OR^1$ or —O—(C=O)—$R^1$ ($R^1$=alkyl, aryl). The following may be used with preference as A: $CH_2$, $CH_2CH_2$, $CH_2CH_2CH_2$, $CH_2CH(CH_3)$, $CH_2CH_2CH_2CH_2$, $CH_2CH_2CH(CH_3)$, $CH_2CH(CH_3)CH_2$, $CH_2CH_2CH_2CH_2CH_2$, $CH_2CH(CH_3)CH_2CH_2$, $CH_2CH_2CH(CH_3)CH_2$, $CH(CH_3)CH_2CH(CH_3)$ or $CH_2CH(CH_3)CH(CH_3)$.

The sulphur-containing silanes of the general formula (I) used may, for example, be the following compounds:
[(MeO)$_3$Si(CH$_2$)$_3$]$_2$S, [(MeO)$_3$Si(CH$_2$)$_3$]$_2$S$_2$, [(MeO)$_3$Si(CH$_2$)$_3$]$_2$S$_3$, [(MeO)$_3$Si(CH$_2$)$_3$]$_2$S$_4$, [(MeO)$_3$Si(CH$_2$)$_3$]$_2$S$_5$, [(MeO)$_3$Si(CH$_2$)$_3$]$_2$S$_6$, [(MeO)$_3$Si(CH$_2$)$_3$]$_2$S$_7$, [(MeO)$_3$Si(CH$_2$)$_3$]$_2$S$_8$, [(MeO)$_3$Si(CH$_2$)$_3$]$_2$S$_9$, [(MeO)$_3$Si(CH$_2$)$_3$]$_2$S$_{10}$, [(MeO)$_3$Si(CH$_2$)$_3$]$_2$S$_{11}$, [(MeO)$_3$Si(CH$_2$)$_3$]$_2$S$_{12}$, [(EtO)$_3$Si(CH$_2$)$_3$]$_2$S, [(EtO)$_3$Si(CH$_2$)$_3$]$_2$S$_2$, [(EtO)$_3$Si(CH$_2$)$_3$]$_2$S$_3$, [(EtO)$_3$Si(CH$_2$)$_3$]$_2$S$_4$, [(EtO)$_3$Si(CH$_2$)$_3$]$_2$S$_5$, [(EtO)$_3$Si(CH$_2$)$_3$]$_2$S$_6$, [(EtO)$_3$Si(CH$_2$)$_3$]$_2$S$_7$, [(EtO)$_3$Si(CH$_2$)$_3$]$_2$S$_8$, [(EtO)$_3$Si(CH$_2$)$_3$]$_2$S$_9$, [(EtO)$_3$Si(CH$_2$)$_3$]$_2$S$_{10}$, [(EtO)$_3$Si(CH$_2$)$_3$]$_2$S$_{11}$, [(EtO)$_3$Si(CH$_2$)$_3$]$_2$S$_{12}$, [(EtO)$_3$Si(CH$_2$)$_3$]$_2$S$_{13}$, [(EtO)$_3$Si(CH$_2$)$_3$]$_2$S$_{14}$, [(C$_3$H$_7$O)$_3$Si(CH$_2$)$_3$]$_2$S, [(C$_3$H$_7$O)$_3$Si(CH$_2$)$_3$]$_2$S$_2$, [(C$_3$H$_7$O)$_3$Si(CH$_2$)$_3$]$_2$S$_3$, [(C$_3$H$_7$O)$_3$Si(CH$_2$)$_3$]$_2$S$_4$, [(C$_3$H$_7$O)$_3$Si(CH$_2$)$_3$]$_2$S$_5$, [(C$_3$H$_7$O)$_3$Si(CH$_2$)$_3$]$_2$S$_6$, [(C$_3$H$_7$O)$_3$Si(CH$_2$)$_3$]$_2$S$_7$, [(C$_3$H$_7$O)$_3$Si(CH$_2$)$_3$]$_2$S$_8$, [(C$_3$H$_7$O)$_3$Si(CH$_2$)$_3$]$_2$S$_9$, [(C$_3$H$_7$O)$_3$Si(CH$_2$)$_3$]$_2$S$_{10}$, [(C$_3$H$_7$O)$_3$Si(CH$_2$)$_3$]$_2$S$_{11}$, [(C$_3$H$_7$O)$_3$Si(CH$_2$)$_3$]$_2$S$_{12}$, [(C$_3$H$_7$O)$_3$Si(CH$_2$)$_3$]$_2$S$_{13}$ or [(C$_3$H$_7$O)$_3$Si(CH$_2$)$_3$]$_2$S$_{14}$ or else

[(C$_{12}$H$_{25}$O)(EtO)$_2$Si(CH$_2$)$_3$]S$_x$[(CH$_2$)$_3$Si(OEt)$_3$], [(C$_{12}$H$_{25}$O)$_2$(EtO)Si(CH$_2$)$_3$]S$_x$[(CH$_2$)$_3$Si(OEt)$_3$], [(C$_{12}$H$_{25}$O)$_3$Si(CH$_2$)$_3$]S$_x$[(CH$_2$)$_3$Si(OEt)$_3$], [(C$_{12}$H$_{25}$O)(EtO)$_2$Si(CH$_2$)$_3$]S$_x$[(CH$_2$)$_3$Si(C$_{12}$H$_{25}$O)(OEt)$_2$], [(C$_{12}$H$_{25}$O)$_2$(EtO)Si(CH$_2$)$_3$]S$_x$[(CH$_2$)$_3$Si(C$_{12}$H$_{25}$O)(OEt)$_2$], [(C$_{12}$H$_{25}$O)$_3$Si(CH$_2$)$_3$]S$_x$[(CH$_2$)$_3$Si(C$_{12}$H$_{25}$O)(OEt)$_2$], [(C$_{12}$H$_{25}$O)(EtO)$_2$Si(CH$_2$)$_3$]S$_x$[(CH$_2$)$_3$Si(C$_{12}$H$_{25}$O)$_2$(OEt)], [(C$_{12}$H$_{25}$O)$_2$(EtO)Si(CH$_2$)$_3$]S$_x$[(CH$_2$)$_3$Si(C$_{12}$H$_{25}$O)$_2$(OEt)], [(C$_{12}$H$_{25}$O)$_3$Si(CH$_2$)$_3$]S$_x$[(CH$_2$)$_3$Si(C$_{12}$H$_{25}$O)$_2$(OEt)], [(C$_{12}$H$_{25}$O)(EtO)$_2$Si(CH$_2$)$_3$]S$_x$[(CH$_2$)$_3$Si(C$_{12}$H$_{25}$O)$_3$], [(C$_{12}$H$_{25}$O)$_2$(EtO)Si(CH$_2$)$_3$]S$_x$[(CH$_2$)$_3$Si(C$_{12}$H$_{25}$O)$_3$], [(C$_{12}$H$_{25}$O)$_3$Si(CH$_2$)$_3$]S$_x$[(CH$_2$)$_3$Si(C$_{12}$H$_{25}$O)$_3$], [(C$_{14}$H$_{29}$O)(EtO)$_2$Si(CH$_2$)$_3$]S$_x$[(CH$_2$)$_3$Si(OEt)$_3$], [(C$_{14}$H$_{29}$O)$_2$(EtO)Si(CH$_2$)$_3$]S$_x$[(CH$_2$)$_3$Si(OEt)$_3$], [(C$_{14}$H$_{29}$O)$_3$Si(CH$_2$)$_3$]S$_x$[(CH$_2$)$_3$Si(OEt)$_3$], [(C$_{14}$H$_{29}$O)(EtO)$_2$Si(CH$_2$)$_3$]S$_x$[(CH$_2$)$_3$Si(C$_{14}$H$_{29}$O)(OEt)$_2$], [(C$_{14}$H$_{29}$O)$_2$(EtO)Si(CH$_2$)$_3$]S$_x$[(CH$_2$)$_3$Si(C$_{14}$H$_{29}$O)(OEt)$_2$], [(C$_{14}$H$_{29}$O)$_3$Si(CH$_2$)$_3$]S$_x$[(CH$_2$)$_3$Si(C$_{14}$H$_{29}$O)(OEt)$_2$], [(C$_{14}$H$_{29}$O)(EtO)$_2$Si(CH$_2$)$_3$]S$_x$[(CH$_2$)$_3$Si(C$_{14}$H$_{29}$O)$_2$(OEt)], [(C$_{14}$H$_{29}$O)$_2$(EtO)Si(CH$_2$)$_3$]S$_x$[(CH$_2$)$_3$Si(C$_{14}$H$_{29}$O)$_2$(OEt)], [(C$_{14}$H$_{29}$O)$_3$Si(CH$_2$)$_3$]S$_x$[(CH$_2$)$_3$Si(C$_{14}$H$_{29}$O)$_2$(OEt)], [(C$_{14}$H$_{29}$O)(EtO)$_2$Si(CH$_2$)$_3$]S$_x$[(CH$_2$)$_3$Si(C$_{14}$H$_{29}$O)$_3$], [(C$_{14}$H$_{29}$O)$_2$(EtO)Si(CH$_2$)$_3$]S$_x$[(CH$_2$)$_3$Si(C$_{14}$H$_{29}$O)$_3$], [(C$_{14}$H$_{29}$O)$_3$Si(CH$_2$)$_3$]S$_x$[(CH$_2$)$_3$Si(C$_{14}$H$_{29}$O)$_3$], [(C$_{16}$H$_{33}$O)(EtO)$_2$Si(CH$_2$)$_3$]S$_x$[(CH$_2$)$_3$Si(OEt)$_3$], [(C$_{16}$H$_{33}$O)$_2$(EtO)Si(CH$_2$)$_3$]S$_x$[(CH$_2$)$_3$Si(OEt)$_3$], [(C$_{16}$H$_{33}$O)$_3$(CH$_2$)Si(CH$_2$)$_3$][(CH$_2$)$_3$Si(C$_3$ (OEt)$_3$], [(C$_{16}$H$_{33}$O)(EtO)$_2$Si(CH$_2$)$_3$]S$_x$[(CH$_2$)$_3$Si(C$_{16}$H$_{33}$O)(OEt)$_2$], [(C$_{16}$H$_{33}$O)$_2$(EtO)Si(CH$_2$)$_3$]S$_x$[(CH$_2$)$_3$Si(C$_{16}$H$_{33}$)(OEt)$_2$], [(C$_{16}$H$_{33}$O)$_3$Si(CH$_2$)]$_3$[S$_x$(CH$_2$)$_3$ (C$_{16}$H$_{33}$O)$_2$(OEt)], [(C$_{16}$H$_{33}$O)(EtO)$_2$Si(CH$_2$)$_3$]S$_x$[(CH$_2$)$_3$Si(C$_{16}$H$_{33}$O)$_2$(OEt)], [(C$_{16}$H$_{33}$O)$_2$ (EtO)Si(CH$_2$)$_3$]S$_x$[(CH$_2$)$_3$Si(C$_{16}$H$_3$)$_2$(OEt)], [(C$_{16}$H$_{33}$O)$_3$Si(CH$_2$)$_3$]S$_x$[(CH$_2$)$_3$Si(C$_{16}$H$_{33}$O)$_2$(OEt)], [(C$_{16}$H$_{33}$O)(EtO)$_2$Si(CH$_2$)$_3$]S$_x$[(CH$_2$)$_3$Si(C$_{16}$H$_{33}$O)$_3$] [(C$_{16}$H$_{70}$)$_3$Si(CH$_2$)$_3$]S$_x$[(CH$_2$)$_3$Si(OEt)][(C$_{16}$H$_{33}$O)$_2$(EtO)Si(CH$_2$)$_3$]S$_x$[(CH$_2$)$_3$Si(C$_{16}$H$_{33}$O)$_3$], [(C$_{18}$H$_{37}$)$_2$(EtO)$_2$Si(CH$_2$)$_3$]S$_x$[(CH$_2$)$_3$Si(OEt)$_3$], [(C$_{18}$H$_{37}$O)$_3$Si(CH$_2$)$_3$]S$_x$[(CH$_2$)$_3$Si(CH$_2$)$_3$Si(OEt)$_3$], [(C$_{18}$H$_{37}$O)(EtO)$_2$Si(CH$_2$)$_3$]S$_x$[(CH$_2$)$_3$Si(C$_{18}$H$_{37}$O)$_2$(OEt)], [(C$_{18}$H$_{37}$O)$_2$(EtO)$_2$Si(CH$_2$)$_3$]S$_x$[(CH$_2$)$_3$Si(C$_{16}$H$_{77}$)$_2$(OEt)], [(C$_{18}$H$_{37}$O)$_3$Si(CH$_2$)$_3$]S$_x$[(CH$_2$)$_3$Si(C$_{18}$H$_{37}$O)$_2$(OEt)$_2$], [(C$_{18}$H$_{37}$O)(EtO)$_2$Si(CH$_2$)$_3$]S$_x$[(CH$_2$)$_3$Si(C$_{18}$H$_{37}$O)$_3$], [(C$_{18}$H$_{37}$O)$_2$(EtO)$_2$Si(CH$_2$)$_3$]S$_x$[(CH$_2$)$_3$Si(C$_{18}$H$_{37}$O)$_3$], [(C$_{18}$H$_{37}$O)$_3$Si(CH$_2$)$_3$]S$_x$[(CH$_2$)$_3$Si(C$_{18}$H$_{37}$O)$_3$], or else generally

[(C$_y$H$_{yx+1}$O)(R)$_2$Si(CH$_2$)$_3$]S$_x$[(CH$_2$)$_3$Si(R)$_3$], [(C$_y$H$_{2y+1}$O)$_2$(R)Si(CH$_2$)$_3$]S$_x$[(CH$_2$)$_3$Si(R)$_3$], [(C$_y$H$_{2y+1}$O)$_3$Si(CH$_2$)$_3$]S$_x$[(CH$_2$)$_3$Si(R)$_3$], [(C$_y$H$_{2y+1}$O)(R)$_2$Si(CH$_2$)$_3$]S$_x$[(CH$_2$)$_3$Si(C$_y$H$_{2y+1}$O)(R)$_2$], [(C$_y$H$_{2y+1}$O)$_2$(R)Si(CH$_2$)$_3$]S$_x$[(CH$_2$)$_3$Si(C$_y$H$_{2y+1}$O)(R)$_2$], [(C$_y$H$_{2y+1}$O)$_3$Si(CH$_2$)$_3$]S$_x$[(CH$_2$)$_3$Si(C$_y$H$_{2y+1}$O)(R)$_2$], [(C$_y$H$_{2y+1}$O)(R)$_2$Si(CH$_2$)$_3$]S$_x$[(CH$_2$)$_3$Si(C$_y$H$_{2y+1}$O)$_2$(R)], [(C$_y$H$_{2y+1}$O)$_2$(R)Si(CH$_2$)$_3$]S$_x$[(CH$_2$)$_3$Si(C$_y$H$_{2y+1}$O)$_2$(R)], [(C$_y$H$_{2y+1}$O)$_3$Si(CH$_2$)$_3$]S$_x$[(CH$_2$)$_3$Si(C$_y$H$_{2y+1}$O)$_2$(R)], [(C$_y$H$_{2y+1}$O)(R)$_2$Si(CH$_2$)$_3$]S$_x$[(CH$_2$)$_3$Si(C$_y$H$_{2y+1}$O)$_3$], [(C$_y$H$_{2y+1}$O)$_2$(R)Si(CH$_2$)$_3$]S$_x$[(CH$_2$)$_3$Si(C$_y$H$_{2y+1}$O)$_3$], or [(C$_y$H$_{2y+1}$O)$_3$Si(CH$_2$)$_3$]S$_x$[(CH$_2$)$_3$Si(C$_y$H$_{2y+1}$O)$_3$], with x=1-14, y=10-24 and R=(MeO) or/and (EtO), or mixtures of the individual silanes mentioned above.

The sulphur-containing silane used may be an organosilicon compound or mixtures of organosilicon compounds of the general formula (II)

$$X^1X^2X^3Si\text{-}A\text{-}S\text{—}SiR^1R^2R^3 \quad (II)$$

in which
$X^1$, $X^2$, $X^3$ and A are each independently as defined in formula (I),
$R^1$, $R^2$, $R^3$ are each independently
$(C_1\text{-}C_{16})$ alkyl, preferably $(C_1\text{-}C_4)$ alkyl, more preferably methyl- and ethyl-,
$(C_1\text{-}C_{16})$ alkoxy, preferably $(C_1\text{-}C_4)$ alkoxy, more preferably methoxy and ethoxy,
$(C_1\text{-}C_{16})$ haloalkyl, aryl, $(C_7\text{-}C_{16})$ aralkyl, —H, halogen or $X^1X^2X^3Si\text{-}A\text{-}S\text{—}$.

The silanes of the general formula (II) used may, for example, be the following compounds:
$(EtO)_3$—Si—$(CH_2)_3$—S—Si$(CH_3)_3$, [$(EtO)_3$—Si—$(CH_2)_3$—S]$_2$Si$(CH_3)_2$, [$(EtO)_3$—Si—$(CH_2)_3$—S]$_3$Si$(CH_3)$, [$(EtO)_3$—Si—$(CH_2)_3$—S]$_2$Si$(OEt)_2$, [$(EtO)_3$—Si—$(CH_2)_3$—S]$_4$Si, $(EtO)_3$—Si—$(CH_2)_3$—S—Si$(OEt)_3$, $(MeO)_3$—Si—$(CH_2)_3$—S—Si$(C_2H_5)_3$, [$(MeO)_3$—Si—$(CH_2)_3$—S]$_2$Si$(C_2H_5)_2$, [$(MeO)_3$—Si—$(CH_2)_3$—S]$_3$Si$(CH_3)$, [$(MeO)_3$—Si—$(CH_2)_3$—S]$_2$Si$(OMe)_2$, [$(MeO)_3$—Si—$(CH_2)_3$—S]$_4$Si, $(MeO)_3$—Si—$(CH_2)_3$—S—Si$(OMe)_3$, $(EtO)_3$—Si—$(CH_2)_2$—CH$(CH_3)$—S—Si$(CH_3)_3$, $(EtO)_3$—Si—$(CH_2)_2$—CH$(CH_3)$—S—Si$(C_2H_5)_3$, $(EtO)_3$—Si—$(CH_2)_2$—CH$(CH_3)$—S—Si$(C_6H_5)_3$ or $(EtO)_3$—Si—$(CH_2)_2$(p-$C_6H_4$)—S—Si$(CH_3)_3$.

The sulphur-containing silane used may be an organosilicon compound or a mixture of organosilicon compounds of the general formula (III)

$$X^1X^2X^3Si\text{-}A\text{-}Sub \quad (III)$$

where $X^1$, $X^2$, $X^3$ and A are each independently as defined in formula (I)
and Sub
is —SH or —SCN.

The sulphur-containing silanes of the general formula (III) used may, for example, be the following compounds:
$(MeO)_3Si$—$(CH_2)_3$—SH, $(MeO)_3Si$—$(CH_2)_3$—SCN, $(EtO)_3Si$—$(CH_2)_3$—SH, $(EtO)_3Si$—$(CH_2)_3$—SCN, $(C_3H_7O)_3Si$—$(CH_2)_3$—SH, $(C_3H_7O)_3Si$—$(CH_2)_3$—SCN, $(C_{12}H_{25}O)_2(MeO)$—Si—$(CH_2)_3$—SH, $(C_{12}H_{25}O)_2(EtO)$—Si—$(CH_2)_3$—SH, $(C_{12}H_{25}O)_2(C_{14}H_{29}O)$—Si—$(CH_2)_3$—SH, $(C_{12}H_{25}O)_2(C_{16}H_{33}O)$—Si—$(CH_2)_3$—SH, $(C_{12}H_{25}O)_2(C_{18}H_{37}O)$—Si—$(CH_2)_3$—SH, $(C_{14}H_{29}O)_2(MeO)$—Si—$(CH_2)_3$—SH, $(C_{14}H_{29}O)_2(EtO)$—Si—$(CH_2)_3$—SH, $(C_{14}H_{29}O)_2(C_{12}H_{25}O)$—Si—$(CH_2)_3$—SH, $(C_{14}H_{29}O)_2(C_{16}H_{33}O)$—Si—$(CH_2)_3$—SH, $(C_{14}H_{29}O)_2(C_1H_{37}O)$—Si—$(CH_2)_3$—SH, $(C_{16}H_{33}O)_2(MeO)$—Si—$(CH_2)_3$—SH, $(C_{16}H_{33}O)_2(EtO)$—Si—$(CH_2)_3$—SH, $(C_{16}H_{33}O)_2(C_{12}H_{25}O)$—Si—$(CH_2)_3$—SH, $(C_{16}H_{33}O)_2(C_{14}H_{29}O)$—Si—$(CH_2)_3$—SH, $(C_{16}H_{33}O)_2(C_{18}H_{37}O)$—Si—$(CH_2)_3$—SH, $(C_{18}H_{37}O)_2(MeO)$—Si—$(CH_2)_3$—SH, $(C_{18}H_{37}O)_2(EtO)$—Si—$(CH_2)_3$—SH, $(C_{18}H_{37}O)_2(C_{12}H_{25}O)$—Si—$(CH_2)_3$—SH, $(C_{18}H_{37}O)_2(C_{14}H_{29}O)$—Si—$(CH_2)_3$—SH, $(C_{18}H_{37}O)_2(C_{16}H_{33}O)$—Si—$(CH_2)_3$—SH, $(C_{12}H_{25}O)_2(C_{14}H_{29}O)$—Si—$(CH_2)_3$—SCN, $(C_{12}H_{25}O)_2(C_{16}H_{33}O)$—Si—$(CH_2)_3$—SCN, $(C_{12}H_{25}O)_2(C_{18}H_{37}O)$—Si—$(CH_2)_3$—SCN, $(C_{14}H_{29}O)_2(C_{12}H_{25}O)$—Si—$(CH_2)_3$—SCN, $(C_{14}H_{29}O)_2(C_{16}H_{33}O)$—Si—$(CH_2)_3$—SCN, $(C_{14}H_{29}O)_2(C_{18}H_{37}O)$—Si—$(CH_2)_3$—SCN, $(C_{16}H_{33}O)_2(C_{12}H_{25}O)$—Si—$(CH_2)_3$—SCN, $(C_{16}H_{33}O)_2(C_{14}H_{29}O)$—Si—$(CH_2)_3$—SCN, $(C_{16}H_{33}O)_2(C_{18}H_{37}O)$—Si—$(CH_2)_3$—SCN, $(C_{18}H_{37}O)_2(C_{12}H_{25}O)$—Si—$(CH_2)_3$—SCN, $(C_{18}H_{37}O)_2(C_{14}H_{29}O)$—Si—$(CH_2)_3$—SCN, $(C_{18}H_{37}O)_2(C_{16}H_{33}O)$—Si—$(CH_2)_3$—SCN,
or mixtures of the abovementioned silanes.

Sulphur-containing silanes used may be oligomers, i.e. oligo- and polysiloxanes, or cooligomers of the silanes of the general formula (I)—(VI) or mixtures thereof. The siloxanes can be obtained by oligomerization or cooligomerization of the corresponding silane compounds of the general formulae (I)—(VI) by addition of water and by the addition of additives known to those skilled in the art in this field.

Sulphur-containing silanes used in the context of the present invention for modification of silica may also be mixtures of silanes, for example mixtures of the silanes of the general formula (I)-(III) or mixtures of the oligomeric or polymeric siloxanes of silanes of the general formula (I)-(III) or mixtures of silanes of the general formula (I)-(III) with mixtures of the oligomeric or polymeric siloxanes of silanes of the general formula (I)-(III).

The sulphur-containing silane used may preferably be $(EtO)_3Si$—$(CH_2)_3$—SCN.

Silicas used may preferably be precipitated or fumed silicas, preferably precipitated silicas.

For example, it is possible to use the Ultrasil 5000 precipitated silica sold by Evonik Industries AG.

The contact between unmodified filler and silane component can be accomplished by means of various technical solutions. This can preferably be effected by means of a suitable mixing unit with internal liquid metering, such units being well known to those skilled in the art in this field. These may, for example, but not exclusively, be mixers as supplied by the companies Drais, Eirich, Forberg, Gericke, Lödige, Ruberg and Zeppelin Reimelt.

The mixing unit can assure a homogeneous distribution, with low abrasion, of the silane used on the silica. The energy input may preferably be low. It is possible to use freefall mixers (for example drum mixers) and mixers having rotating tools and low particle stress (Froude number <1) for this purpose.

In the process according to the invention, 10-250 parts by weight of silica may be reacted with 0.1-50 parts by weight, preferably 0.5-15 parts by weight, of silane.

In the process according to the invention, the pressure, which is also called working pressure, may generally be between 1 and 100 bar, preferably between 1 and 20 bar, more preferably between 1 and 15 bar.

The temperature (working temperature) at which the process can be conducted is between 0 and 300° C., preferably between 0 and 200° C., more preferably between 10 and 130° C.

During the reaction, an additive can additionally be introduced.

Additives used may be stearic acid, lactic acid, citric acid or polyethylene glycol.

The silica which has been mixed with the silane can be circulated continuously with a suitable stirrer unit in the high-pressure apparatus or the high-pressure vessel. In this case, the stirrer speed can be adjusted with respect to the prevailing temperature and the pressure that prevails at that temperature.

Stirrer units used may be reciprocating stirrers, paddle stirrers, beam stirrers, perforated beam stirrers, cross-beam stirrers, anchor stirrers, gate stirrers, paddle rollers, propeller stirrers, screw stirrers, turbine stirrers, disc stirrers, planetary stirrers, circulation mixers or impeller stirrers.

The stirrer unit can work at 1-100 revolutions, preferably 1-50 revolutions, reciprocating movements or cycles, per minute.

After the surface modification, the silane-modified silica may be subjected to an evacuation or decompression stage with removal of the additives added or of a portion of the additives added from the end product.

The evacuation or decompression stage can be conducted within a period between 1 min and 180 min, preferably between 1 min and 120 min, more preferably between 1 min and 60 min.

The evacuation or decompression stage can be conducted at temperatures between 1 and 300° C., preferably between 1 and 200° C., more preferably between 1 and 150° C., and most preferably at temperatures between 1 and 130° C.

The inventive silane-modified silica can be subjected to an additional compaction or processing step.

The inventive silane-modified silica can be obtained by the process according to the invention.

The silane-modified silica can be used in paints, lacquers, printing inks, coatings, adhesives and lubricants, cosmetics, toothpastes, building auxiliaries, or as a filler in vulcanizable rubbers, silicones or plastics.

The invention further provides rubber mixtures which are characterized in that they comprise rubber, the inventive silane-modified silica, optionally precipitated silica and/or carbon black and/or further rubber auxiliaries.

For production of inventive rubber mixtures, it is possible to use natural rubber or synthetic rubbers. Preferred synthetic rubbers are described, for example, in W. Hofmann, Kautschuktechnologie [Rubber Technology], Genter Verlag, Stuttgart 1980. They include, inter alia, polybutadiene (BR), polyisoprene (IR), styrene/butadiene copolymers having styrene contents of 1% to 60%, preferably 5% to 50% by weight (E- or S-SBR), isobutylene/isoprene copolymers (IIR), butadiene/acrylonitrile copolymers having acrylonitrile contents of 5% to 60%, preferably 10% to 50% by weight (NBR), chloroprene (CR), ethylene/propylene/diene copolymers (EPDM), and mixtures of these rubbers.

The inventive rubber mixtures may comprise further rubber auxiliary products, for example reaction accelerators, reaction retardants, ageing stabilizers, other stabilizers, processing auxiliaries, plasticizers, waxes, metal oxides, and activators such as triethanolamine, polyethylene glycol or hexanetriol, organically modified silanes and other rubber auxiliary products known in the rubber industry.

The rubber mixture may additionally comprise alkylsilanes or/and silicone oils.

The rubber auxiliaries can be used in customary amounts guided by factors including the end use. Typical amounts are, for example, amounts of 0.1 to 50% by weight based on rubber.

Crosslinkers used may be sulphur, organic sulphur donors or free-radical formers. The inventive rubber mixtures may additionally comprise vulcanization accelerators.

Examples of suitable vulcanization accelerators are mercaptobenzothiazoles, sulphenamides, guanidines, thiurams, dithiocarbamates, thioureas and thiocarbonates.

The vulcanization accelerators and crosslinkers can be used in amounts of 0.1% to 10% by weight, preferably 0.1% to 5% by weight, based on rubber.

The blending of the rubbers with the inventive silane-modified silica, optionally with precipitated silica and/or carbon black and/or further rubber auxiliaries, can be performed in customary mixing units, such as rollers, internal mixers and mixing extruders. Typically, it is possible to produce such rubber mixtures in internal mixers, in which case the rubbers, the inventive silane-modified silica, optionally the precipitated silica and/or carbon black and/or further rubber auxiliaries are first mixed in at 100 to 170° C. in one or more successive thermomechanical mixing stages. The addition sequence and the addition time for the individual components may have a crucial effect on the mixture properties obtained. The rubber mixture thus obtained can then be admixed with the crosslinking chemicals in a known manner in an internal mixer or on a roller at 40-110° C., and processed to what is called the crude mixture for the subsequent process steps, for example shaping and vulcanization.

The vulcanization of the inventive rubber mixtures can be effected at temperatures of 80 to 200° C., preferably 130 to 180° C., optionally under a pressure of 10 to 200 bar.

The inventive rubber mixtures are suitable for production of mouldings from rubber, for example for the production of pneumatic tyres for passenger and heavy goods vehicles, tyre treads for passenger and heavy goods vehicles, tyre constituents for passenger and heavy goods vehicles, for example sidewall, inner liner and carcass, cable sheaths, hoses, drive belts, conveyor belts, roll covers, pedal cycle and motorcycle tyres and constituents thereof, shoe soles, gasket rings, profiles and damping elements.

The inventive silane-modified silicas, compared to the products known from the prior art, have excellent dispersibility and improved rubber properties, for example abrasion, vulcanization characteristics and Mooney viscosity.

EXAMPLES

Sears Number

The Sears numbers are determined based on G. W. Sears, Analyt. Chemistry 12 (1956) 1982, by the following method:

Before the titration, the filler is ground in a mill, in the course of which it is homogenized and comminuted. 2.5 g of the sample thus obtained are admixed with 60 ml of methanol in a 250 ml titration vessel and, as soon as the solid has been fully wetted, a further 40 ml of water are added to the suspension.

A stirrer (Ultra-Turrax) is used to disperse the suspension for 30 sec, which is then diluted with a further 100 ml of water. The suspension is equilibrated to 25° C. over at least 20 minutes.

The titration is effected on a titroprocessor with pH electrode (e.g. DL 67, Mettler Toledo with DG 111 SC electrode), as follows:

first stir for 120 sec;
adjust suspension to pH 6 with 0.1 N potassium hydroxide or hydrochloric acid;
meter in 20 ml of NaCl solution (250 g/l);
titrate with 0.1 N KOH from pH 6 to pH 9;
convert the result to 5 g of silica, i.e. to consumption of 0.1 N KOH in ml per 5 g of silica to reach pH 9 from pH 6.

The present determination is a further development, increase in precision and improvement on the process described in G. W. Sears, Analyt. Chemistry 12 (1956) 1982.

BET Surface Area

The samples are dried at 105° C. for 15-20 h and the BET surface area is determined to DIN 66131 (volumetric method).

Particle Size Distribution

All the samples were screened through a 500 μm screen. The particle size distribution of the samples is determined by laser diffraction analysis with ultrasound treatment for 3 minutes using a Cilas 1064 L (from Quantachrome) in accordance with the commonly known rules and operating instructions.

The sample preparation for the analysis (purging etc.) by means of the Cilas 1064 L laser diffraction unit (S/N 152, from Quantachrome; measurement range 0.04-500 μm and 400 ml wet dispersion unit with integrated ultrasound) is effected in the case of unmodified silicas with the aid of 0.05% m/m tetrasodium diphosphate in demineralized water as dispersion liquid, and in the case of silane-modified silicas with an ethanol/water mixture (volume ratio 1:1) as dispersion liquid.

Before the start of the analysis, the laser diffraction system has to warm up for 2 hours. Thereafter, the Cilas 1064 L is purged two to four times.

The material to be analysed is screened through a 500 μm screen. From the <500 μm fraction, about 0.5-1.0 g of sample is required for the analysis, depending on the nature of the material.

The following parameters relevant for the particle analysis should be set:

Ultrasound during dispersion: 180 seconds
Number of measurements: 1
Pump speed: 120 rpm (fixed on the instrument)
Stirrer speed: 300 rpm (fixed on the instrument)
Optical model: Fraunhofer (fixed on the instrument)

After conducting the background measurement, the silica sample is added.

After stirring the silica suspension for 60 seconds, followed by ultrasound treatment for 3 minutes, the analysis is effected while the suspension is being pumped in circulation. The target measurement concentration for the analysis is 120+/−30. If the measurement concentration is below the target concentration level, the analysis should be stopped and the sample weight increased. If the measurement concentration is exceeded, there is the possibility of automatic dilution by the Cilas 1064 L.

The software calculates the particle size distribution from the raw data curve with the aid of the Fraunhofer theory.

Sulphur Content

For the determination of the average sulphur content of the samples, samples are taken from the autoclave inserts at both ends of the insert and in the middle, and the sulphur content thereof is determined by known processes, by:

Schöniger digestion in an oxygen atmosphere (cf. F. Ehrenberger, S. Gorbauch, "Methoden der organischen Elementar-und Spurenanalyse" [Methods of organic elemental and trace analysis], Verlag Chemie GmbH, Weinheim/Bergstrasse, 1973) and downstream ion chromatography analysis (Metrohm 690 ion chromatograph; Hamilton PRP X-100 column; eluent: 2 mmol salicylate buffer, pH 7) to DIN ISO 10304-2.

The average sulphur content of the overall sample is then obtained as the arithmetic mean of the 3 values thus determined for the individual samples.

Water Content

The water content of the samples is determined as follows:

10 g of the silanized silica are comminuted with a coffee grinder for 15 seconds and then the water content is determined by the known rules familiar to the person skilled in the art with a Karl Fischer titrator (from Metrohm, 720 KFS Titrino) and the Karl Fischer titration chemicals No. 1.09241, No. 1.09243 and No. 1.06664 available from Merck (disodium tartrate dihydrate).

Carbon Content

The carbon content of the samples is determined by known standard methods by means of a LECO CS-244 carbon/sulphur determinator.

The silica used is Perkasil KS 300 from Grace.

Example 1: Preparation of Silica A

A stainless steel reactor with propeller stirring system and jacket heating is initially charged with 1510 l of water and 46 kg of waterglass (density 1.348 kg/l, 27.0% SiO2, 8.05% Na$_2$O). Subsequently, while stirring vigorously at 92° C. for 90 minutes, 6.655 kg/min of the abovementioned waterglass and about 0.832 kg/min of sulphuric acid (density 1.83 kg/l, 96% H$_2$SO$_4$) are metered in. This metered addition of sulphuric acid is regulated such that an alkali number of 7 prevails in the reaction medium. Subsequently, the addition of waterglass is stopped and further sulphuric acid is fed in until a pH of 8.5 (measured at room temperature) is attained. After a rest period of about 30 min, further sulphuric acid is metered in until a pH of 4.5 has been attained. The resulting suspension is filtered with a membrane filter press and washed with water and dried.

Example 2: Preparation of Silica B

A stainless steel reactor with propeller stirring system and jacket heating is initially charged with 1550 l of water and 141.4 kg of waterglass (density 1.348 kg/l, 27.0% SiO2, 8.05% Na$_2$O). Subsequently, while stirring vigorously at 92° C. for 100 minutes, 5.505 kg/min of the abovementioned waterglass and about 0.65 kg/min of sulphuric acid (density 1.83 kg/l, 96% H$_2$SO$_4$) are metered in. This metered addition of sulphuric acid is regulated such that an alkali number of prevails in the reaction medium. Subsequently, the addition of waterglass is stopped and further sulphuric acid is fed in until a pH of 9.0 (measured at room temperature) is attained. The addition of sulphuric acid is stopped and the suspension obtained is stirred at 90° C. for a further 60 minutes. Thereafter, the addition of sulphuric acid is restarted and a pH of 3.5 (measured at room temperature) is established. The resulting suspension is filtered with a membrane filter press and then dried.

Table 1 shows the analytical data of the silicas and the particle sizes (Table 2).

TABLE 1

| | Unit | Perkasil KS 300 | Silica A | Silica B |
|---|---|---|---|---|
| BET | m$^2$/g | 125 | 127 | 120 |
| CTAB | m$^2$/g | 122 | 122 | 112 |
| pH | | 7.2 | 7.2 | 6.5 |
| Moisture content | % | 5.5 | 5.5 | 6.4 |

TABLE 2

| | Unit | Perkasil KS 300 | Silica A | Silica B |
|---|---|---|---|---|
| d5 | μm | 3.9 | 5.85 | 6.14 |
| d50 | μm | 12.6 | 19.98 | 21.39 |
| d95 | μm | 35.1 | 40.89 | 42.45 |
| dmedian | μm | 15.2 | 21.11 | 22.34 |

For the production of the silane-modified silicas, an FM40 Henschel mixer fluid mixer from the Zeppelin Reimelt company in Kassel is used. The Henschel mixer consists of a 40 liter mixing vessel with hinged lid, both provided with jackets for temperature control medium (oil). The mixing tools are driven from beneath by means of an electric motor with a drive belt. The mixing tool speed is variable up to 2500 rpm and is set by means of a handwheel.

Si 69 is bis(triethoxysilylpropyl) tetrasulphide and Si 264 is 3-thiocyanatopropyltriethoxysilane from Evonik Industries AG.

Example 3: Preparation of the Inventive Silane-Modified Silica (Silica A+Si 264)

The Henschel mixer is initially charged with the appropriate amount of filler and the mixer is switched on. The mixing tool speed is set to the appropriate value. The silane is sprayed into the mixer by means of an ultrasound nozzle. Subsequently, the mixer outlet valve is opened and the product is discharged from the mixer.

The mixing conditions are listed in Table 3. The silica used is silica A (Example 1), and the silane Si 264.

Example 4: Preparation of the Inventive Silane-Modified Silica (Silica A+Si 69)

The preparation is effected analogously to Example 3. The mixing conditions are listed in Table 3. The silica used is silica A (Example 1), and the silane Si 69.

Example 5: Preparation of the Inventive Silane-Modified Silica (Silica B+Si 264)

The preparation is effected analogously to Example 3. The mixing conditions are listed in Table 3. The silica used is silica B (Example 2), and the silane Si 264.

Example 6: Preparation of the Inventive Silane-Modified Silica (Silica B+Si 69)

The preparation is effected analogously to Example 3. The mixing conditions are listed in Table 3. The silica used is silica B (Example 2), and the silane Si 69.

Example 7: Preparation of Silane-Modified Silica (Perkasil KS 300P Silica+Si 264)

The preparation is effected analogously to Example 3. The mixing conditions are listed in Table 3. The silica used is Perkasil KS 300P, and the silane Si 264.

Example 8: Preparation of Silane-Modified Silica (Perkasil KS 300P Silica+Si 69)

The preparation is effected analogously to Example 3. The mixing conditions are listed in Table 3. The silica used is Perkasil KS 300P, and the silane Si 69.

TABLE 3

| | Example 3 | Example 4 | Example 5 | Example 6 | Example 7 | Example 8 |
|---|---|---|---|---|---|---|
| Flow temperature (° C.) | 20 | 20 | 20 | 20 | 20 | 20 |
| Amount of filler (kg) | 3 | 3 | 3 | 3 | 3 | 3 |
| Amount of silane (kg) | 0.330 | 0.270 | 0.330 | 0.270 | 0.330 | 0.270 |
| Mixing temperature (° C.) | (55) | (55) | (55) | (55) | (55) | (55) |
| Stirrer speed (rpm) | 1500 | 1500 | 1500 | 1500 | 1500 | 1500 |
| Nozzle diameter (mm) | (0.5) | (0.5) | (0.5) | (0.5) | (0.5) | (0.5) |
| Atomization pressure (bar) | 40 | 40 | 40 | 40 | 40 | 40 |
| Mixing time (min) | 7 | 7 | 7 | 7 | 7 | 7 |

Table 4 shows the particle sizes of the silane-modified silicas.

TABLE 4

| | Unit | Example 3 | Example 4 | Example 5 | Example 6 | Example 7 | Example 8 |
|---|---|---|---|---|---|---|---|
| d5 | μm | 4.47 | 4.21 | 4.13 | 4.31 | 3.84 | 3.87 |
| d50 | μm | 19.70 | 19.31 | 20.65 | 20.16 | 15.74 | 15.57 |
| d95 | μm | 43.33 | 43.55 | 46.20 | 47.12 | 46.17 | 46.46 |
| Dmedian | μm | 21.02 | 20.76 | 21.84 | 21.88 | 19.47 | 19.51 |
| Sulphur content | % by weight | 1.21 | 1.84 | 1.21 | 1.84 | 1.21 | 1.84 |

Example 9: Rubber Mixtures

The formulation used for the rubber mixtures is specified in Table 5 below. The unit phr means parts by weight based on 100 parts of the raw rubber used. The general method for producing rubber mixtures and vulcanizates thereof is described in the following book: "Rubber Technology Handbook", W. Hofmann, Hanser Verlag 1994.

TABLE 5

| Mixture | Amount [phr] 1 | Amount [phr] 2 | Amount [phr] 3 | Amount [phr] 4 | Amount [phr] 5 | Amount [phr] 6 | Amount [phr] 7 | Amount [phr] 8 |
|---|---|---|---|---|---|---|---|---|
| 1st stage | | | | | | | | |
| Buna® EP G 5455 | 150 | 150 | 150 | 150 | 150 | 150 | 150 | 150 |
| Perkasil KS 300 | 60 | 60 | 0 | 0 | 0 | 0 | 0 | 0 |
| Inv. Example 3 | 0 | 0 | 61 | 0 | 0 | 0 | 0 | 0 |
| Inv. Example 4 | 0 | 0 | 0 | 62 | 0 | 0 | 0 | 0 |
| Inv. Example 5 | 0 | 0 | 0 | 0 | 61 | 0 | 0 | 0 |
| Inv. Example 6 | 0 | 0 | 0 | 0 | 0 | 62 | 0 | n |
| Comparative Example 7 | 0 | 0 | 0 | 0 | 0 | 0 | 62 | 0 |
| Comparative Example 8 | 0 | 0 | 0 | 0 | 0 | 0 | 0 | 62 |
| Si 264 | 1 | 0 | 0 | 0 | 0 | 0 | 0 | 0 |
| Si 69® | 0 | 2 | 0 | 0 | 0 | 0 | 0 | 0 |
| Stearic acid | 2 | 2 | 2 | 2 | 2 | 2 | 2 | 2 |
| ZnO | 4 | 4 | 4 | 4 | 4 | 4 | 4 | 4 |
| Vivatec 500 | 30 | 30 | 30 | 30 | 30 | 30 | 30 | 30 |
| Vulkanox 4020/LG | 1.5 | 1.5 | 1.5 | 1.5 | 1.5 | 1.5 | 1.5 | 1.5 |
| 2nd stage | | | | | | | | |
| Stage 1 batch | | | | | | | | |
| Vulkacit Mercapto C | 1 | 1 | 1 | 1 | 1 | 1 | 1 | 1 |
| Robac TBED | 0.8 | 0.8 | 0.8 | 0.8 | 0.8 | 0.8 | 0.8 | 0.8 |
| Rhenocure TP/S | 2 | 2 | 2 | 2 | 2 | 2 | 2 | 2 |
| Rhenogran DPG-80 | 2.5 | 2.5 | 2.5 | 2.5 | 2..5 | 2.5 | 2.5 | 2.5 |
| Sulphur | 1.5 | 1.5 | 1.5 | 1.5 | 1.5 | 1.5 | 1.5 | 1.5 |

The polymer Buna® EP G 5455 is an ethylene-propylene terpolymer having a moderate unsaturation level (ENB content=4.3) containing 50 phr paraffinic oil from Lanxess. The polymer has a Mooney viscosity (ML 1+4/125° C./ML (1+8)) of 46. The mineral oil used is Vivatec 500 from the H&R Group. Vulkanox 4020 is 6PPD from Lanxess. Vulkacit Mercapto C is a commercial product from Lanxess.

Robac TBED is a commercial product from Robinson Brothers. Rhenocure TP/S and Rhenogran DPG-80 are commercial products from Rheinchemie.

The rubber mixtures are produced in an internal mixer according to the mixing method in Table 6.

TABLE 6

| Stage 1 | |
|---|---|
| Settings | |
| Mixing unit | Werner & Pfleiderer N type |
| Speed | 60 min$^{-1}$ |//

TABLE 6-continued

| Ram pressure | 5.5 bar |
|---|---|
| Capacity | 1.60 l |
| Fill level | 0.70 |
| Flow temp. | 60° C. |
| Mixing process | |
| 0 to 1 min | Buna EP G 5455 |
| | ⅓ silica or silanized silica, |
| | optionally silane, ZnO, stearic acid, |
| | Vulkanox |

TABLE 6-continued

| | |
|---|---|
| 1 to 2 min | clean and mix |
| 2 to 3 min | ⅓ silica or silanized silica, ½ Vivatec |
| 3 to 4 min | clean and mix |
| 4 to 5 min | ⅓ silica or silanized silica, ½ Vivatec |
| 5 to 6 min | clean and mix |
| 6 to 7 min | mix |
| 7 min | discharge |
| Batch temp. | 90-130° C. |
| Storage | 4 h at room temperature |

Stage 2

| Settings | |
|---|---|
| Mixing unit | As in stage 1 except: |
| Flow temp. | 40° C. |
| Speed | 50 min$^{-1}$ |
| Fill level | 0.68 |

Mixing process

| | |
|---|---|
| 0 to 2 min | Stage 1 batch, accelerator, sulphur |
| 2 min | discharge |
| Batch temp. | 80-100° C. |
| Storage | 4 h at room temperature |

Table 7 summarizes the methods for rubber testing.

TABLE 7

| Physical testing | Standard/conditions |
|---|---|
| ML 1 + 4, 100° C., 3rd stage | DIN 53523/3, ISO 667 |
| Vulkameter test, 165° C. | DIN 53529/3, ISO 6502 |
| Dmax − Dmin [dNm] | |
| t10% and t90% [min] | |
| Ring tensile test, 23° C. | DIN 53504, ISO 37 |
| Tensile strength [MPa] | |
| Stress values [MPa] | |
| Elongation at break [%] | |
| Shore A hardness, 23° C. [SH] | DIN 53 505 |
| Viscoelastic properties | DIN 53 513, ISO 2856 |
| 0 and 60° C., 16 Hz, initial force 50N | |
| and amplitude force 25 N | |
| Dynamic modulus E* [MPa] | |
| Loss factor tan δ [ ] | |
| Ball rebound, 23° C., 60° C. [%] | ASTM D 5308 |
| DIN abrasion, force 10N [mm$^3$] | DIN 53 516 |

The results of the rubber tests are compiled in Table 8.

TABLE 8

| Mixture | | 1 | 2 | 3 | 4 | 5 | 6 | 7 | 8 |
|---|---|---|---|---|---|---|---|---|---|
| ML(1 + 4) 100° C. 1st stage | MU | 76 | 77 | 64 | 63 | 63 | 64 | 67 | 71 |
| ML(1 + 4) 100° C. 2nd stage | MU | 68 | 66 | 61 | 60 | 59 | 60 | 64 | 63 |
| Energy input, 1st stage | [kWh] | 0.51 | 0.50 | 0.46 | 0.44 | 0.45 | 0.41 | 0.43 | 0.41 |
| Specific energy/ 1st stage | [kWh/Kg] | 0.45 | 0.44 | 0.41 | 0.38 | 0.39 | 0.35 | 0.38 | 0.36 |
| MDR: 165° C.; 0.5° | | | | | | | | | |
| t20% | min | 0.6 | 1.0 | 0.6 | 0.7 | 0.7 | 0.7 | 0.5 | 0.5 |
| t90% | min | 6.3 | 7.6 | 4.8 | 6.1 | 5.2 | 5.5 | 4.8 | 6.1 |
| t80%-t20% | min | 3.5 | 4.2 | 2.6 | 3.3 | 2.7 | 2.9 | 2.6 | 3.3 |
| 100% modulus | MPa | 1.1 | 1.3 | 0.9 | 1.1 | 1.0 | 1.2 | 0.9 | 1.1 |
| 300% modulus | MPa | 3.8 | 4.6 | 4.5 | 5.9 | 4.8 | 6.3 | 4.5 | 5.9 |
| 300%/100% modulus | — | 3.5 | 3.5 | 4.5 | 5.4 | 4.8 | 5.3 | 5.0 | 5.4 |
| Elongation at break | % | 491 | 469 | 584 | 413 | 505 | 355 | 584 | 413 |
| Shore A hardness | SH | 46 | 48 | 45 | 48 | 46 | 49 | 45 | 48 |
| DIN abrasion, 10N | mm$^3$ | 192 | 193 | 146 | 128 | 133 | 134 | 146 | 128 |
| Ball rebound, RT | % | 72.9 | 72.9 | 67.8 | 68.6 | 67.5 | 69.7 | 67.8 | 68.6 |
| Ball rebound, 70° C. | % | 80.5 | 79.4 | 75.1 | 79.6 | 74.2 | 79.8 | 75.1 | 79.6 |
| MTS, 16 Hz, 50N+/−25N | | | | | | | | | |
| E*, 0° C. | MPa | 5.4 | 5.6 | 5.6 | 5.5 | 5.6 | 5.6 | 5.6 | 5.5 |
| E*, 60° C. | MPa | 5.5 | 5.9 | 5.4 | 5.7 | 5.4 | 5.8 | 5.4 | 5.7 |
| Dispersion topography Sum of the peaks | — | 344 | 357 | 128 | 134 | 188 | 205 | 336 | 386 |
| Peak area (topo) | % | 25.6 | 27.2 | 10.6 | 11.3 | 13.2 | 15.5 | 24.0 | 26.2 |

As is apparent from Table 8, mixtures 3-6 show a significant improvement in the energy required during the mixing operation. The Mooney viscosities of the mixtures with the inventive silanized silicas are much improved.

The mixtures with the inventive silanized silicas show better (quicker) vulcanization characteristics combined with simultaneous retention of scorch resistance and improved abrasion resistance.

The modulus, elongation at break and dynamic data of the mixtures with the inventive silanized silicas are at the same level as the comparative mixtures.

The invention claimed is:

1. A silane-modified silica,
wherein the BET surface area is 40 to 155 m²/g;
the sulphur content is between 0.05% and 25% by weight relative to the total weight of the silane-modified silica; and
the particle size $d_5$ is ≥4 μm and $d_{50}$ is ≥16 μm.

2. The silane-modified silica according to claim 1, wherein the BET surface area is 50 to 135 m²/g.

3. The silane-modified silica according to claim 1 wherein the sulphur content is between 0.05% and 10% by weight relative to the total weight of the silane-modified silica.

4. The silane-modified silica according to claim 1 comprising SCN groups.

5. A process for preparing the silane-modified silica according to claim 1, the process comprising:
reacting at least one silica having a BET surface area of 40 to 150 m²/g and a particle size $d_5$ of ≥4 μm and $d_{50}$ of ≥16 μm with at least one sulphur-containing silane.

6. The process for preparing the silane-modified silica according to claim 5, wherein the sulphur-containing silane is an organosilicon compound or a mixture of organosilicon compounds of the general formula (I)

$$\text{Z-A-S}_x\text{-A-Z} \qquad \text{(I)}$$

wherein,
x is a number from 1 to 14;
Z is $\text{SiX}^1\text{X}^2\text{X}^3$;
wherein, $X^1$, $X^2$, $X^3$ are each independently a hydrogen (—H), a halogen or hydroxyl (—OH), an alkyl substituent, an alkyl acid substituent $(C_yH_{2y+1})$—C(=O)O— wherein y is 1 to 14, an alkenyl acid substituent or a substituted alkyl or alkenyl acid substituent, a linear or branched, cyclic hydrocarbon chain having 1-8 carbon atoms, a cycloalkyl radical having 5-12 carbon atoms, a benzyl radical or a halogen- or alkyl-substituted phenyl radical, an alkoxy group having linear or branched hydrocarbon chains having ($C_{1-24}$) atoms, an alkoxy group having linear or branched polyether chains having ($C_{1-24}$) atoms, a cycloalkoxy group having ($C_{5-12}$) atoms, or a halogen- or alkyl-substituted phenoxy group or a benzyloxy group; and
A is a branched or unbranched, saturated or unsaturated, aliphatic, aromatic or mixed aliphatic/aromatic divalent $C_1$-$C_{30}$-comprising hydrocarbon chain.

7. The process for preparing the silane-modified silica according to claim 5, wherein the sulphur-containing silane is an organosilicon compound or a mixture of organosilicon compounds of the general formula (II)

$$X^1X^2X^3\text{Si-A-S—SiR}^1R^2R^3 \qquad \text{(II)}$$

wherein,
$X^1$, $X^2$, $X^3$ are each independently a hydrogen (—H), a halogen or hydroxyl (—OH), an alkyl substituent, an alkyl acid substituent $(C_yH_{2y+1})$—C(=O)O— wherein y is 1 to 14, an alkenyl acid substituent or a substituted alkyl or alkenyl acid substituent, a linear or branched, cyclic hydrocarbon chain having 1-8 carbon atoms, a cycloalkyl radical having 5-12 carbon atoms, a benzyl radical or a halogen- or alkyl-substituted phenyl radical, an alkoxy group having linear or branched hydrocarbon chains having ($C_{1-24}$) atoms, an alkoxy group having linear or branched polyether chains having ($C_{1-24}$) atoms, a cycloalkoxy group having ($C_{5-12}$) atoms, or a halogen- or alkyl-substituted phenoxy group or a benzyloxy group;
A is a branched or unbranched, saturated or unsaturated, aliphatic, aromatic or mixed aliphatic/aromatic divalent $C_1$-$C_{30}$-comprising hydrocarbon chain; and
$R^1$, $R^2$, $R^3$ are each independently a ($C_1$-$C_{16}$) alkyl, a ($C_1$-$C_{16}$) alkoxy, a ($C_1$-$C_{16}$) haloalkyl, an aryl, a ($C_7$-$C_{16}$) aralkyl, —H, a halogen or $X^1X^2X^3\text{Si-A-S—}$.

8. The process for preparing the silane-modified silica according to claim 5, wherein the sulphur-containing silane is an organosilicon compound or a mixture of organosilicon compounds of the general formula (III)

$$X^1X^2X^3\text{Si-A-Sub} \qquad \text{(III)}$$

wherein,
$X^1$, $X^2$, $X^3$ are each independently as a hydrogen (—H), a halogen or hydroxyl (—OH), an alkyl substituent, an alkyl acid substituent $(C_yH_{2y+1})$—C(=O)O— wherein y is 1 to 14, an alkenyl acid substituent or a substituted alkyl or alkenyl acid substituent, a linear or branched, cyclic hydrocarbon chain having 1-8 carbon atoms, a cycloalkyl radical having 5-12 carbon atoms, a benzyl radical or a halogen or alkyl-substituted phenyl radical, an alkoxy group having linear or branched hydrocarbon chains having ($C_{1-24}$) atoms, an alkoxy group having linear or branched polyether chains having ($C_{1-24}$) atoms, a cycloalkoxy group having ($C_{5-12}$) atoms, or a halogen- or alkyl-substituted phenoxy group or a benzyloxy group;
A is a branched or unbranched, saturated or unsaturated, aliphatic, aromatic or mixed aliphatic/aromatic divalent $C_1$-$C_{30}$-comprising hydrocarbon chain; and
Sub is —SH or —SCN.

9. The process for preparing the silane-modified silica according to claim 8, wherein the organosilicon compounds are of the formula $(\text{EtO})_3\text{Si—(CH}_2)_3\text{—SCN}$.

10. A rubber mixture comprising rubber, the silane-modified silica according to claim 1, and optionally at least one member selected from the group consisting of precipitated silica, carbon black, and rubber auxiliaries.

11. A process comprising producing pneumatic tyres for passenger and heavy goods vehicles, tyre treads for passenger and heavy goods vehicles, tyre constituents for passenger and heavy goods vehicles, cable sheaths, hoses, drive belts, conveyor belts, roller coverings, pedal cycle and motorcycle tyres and constituents thereof, shoe soles, gasket rings, profiles and damping elements comprising the rubber mixture according to claim 10.

12. The rubber mixture of claim 10, which has a reduced Mooney viscosity relative to a rubber mixture lacking the silane-modified silica.

13. The rubber mixture of claim 10, which has an improved dispersancy as measured by dispersion topography and a decreased vulcanization energy input relative to a rubber mixture lacking the silane-modified silica.

14. The rubber mixture of claim 10, which has an improved abrasion resistance relative to a rubber mixture lacking the silane-modified silica.

15. A paint, a lacquer, a printing ink, a coating, an adhesive, a lubricant, a cosmetic, a toothpaste, a building auxiliary, or a filler in vulcanizable rubber, silicones or plastics comprising the silane-modified silica according to claim 1.

16. A rubber mixture comprising rubber, the silane-modified silica according to claim 1, and at least one of precipitated silica, carbon black, and further rubber auxiliaries.

17. The silane-modified silica according to claim 1 obtained by reaction of at least one silica with at least one sulphur containing silane that is an organosilicon compound or a mixture of organosilicon compounds of the formula $(EtO)_3Si-(CH_2)_3-SCN$.

* * * * *